United States Patent [19]

Pralus et al.

[11] Patent Number: 4,994,583

[45] Date of Patent: * Feb. 19, 1991

[54] PROCESS FOR THE PREPARATION OF EPSILON-CAPROLACTONE

[75] Inventors: Michéle Pralus, Saint Cyr Au Mont D'Or; Jean-Claude Lecoq, Chaponost; Jean-Pierre Schirmann, Oullins, all of France

[73] Assignee: Produits Chimiques Uging Kuhlmann, Courbevoie, France

[ * ] Notice: The portion of the term of this patent subsequent to Apr. 26, 2005 has been disclaimed.

[21] Appl. No.: 377,806

[22] Filed: Jul. 12, 1989

Related U.S. Application Data

[63] Continuation of Ser. No. 929,888, Nov. 13, 1986, abandoned, which is a continuation of Ser. No. 653,667, Sep. 21, 1984, abandoned, which is a continuation of Ser. No. 457,914, Jan. 14, 1983, abandoned.

[30] Foreign Application Priority Data

Jan. 15, 1982 [FR] France ............................ 8200564

[51] Int. Cl.⁵ .......................................... C07D 313/04
[52] U.S. Cl. .................................................. 549/272
[58] Field of Search ........................................ 549/272

[56] References Cited

U.S. PATENT DOCUMENTS

| | | | |
|---|---|---|---|
| 3,064,008 | 11/1962 | Phillips et al. | 549/272 |
| 3,523,955 | 8/1970 | Lantz et al. | |
| 3,766,212 | 10/1973 | Waldmann et al. | 549/272 |
| 4,338,260 | 6/1982 | Shirmann | 549/272 |
| 4,341,709 | 7/1982 | Hofen et al. | 549/272 |
| 4,740,603 | 4/1988 | Lecog et al. | 549/272 |

FOREIGN PATENT DOCUMENTS 2464947 3/1981 France .

OTHER PUBLICATIONS

V. M. Vishnyakov et al., Journal of Applied Chemistry, U.S.S.R., vol. 46, (9), pp. 2035-2041 (1976).

Primary Examiner—Richard L. Raymond
Assistant Examiner—Mark W. Russell
Attorney, Agent, or Firm—Pennie & Edmonds

[57] ABSTRACT

Process for manufacturing $\Sigma$- caprolactone by oxidation of cyclohexanone by means of a crude $C_2$-$C_4$ percarboxylic acid solution, resulting from the reaction of hydrogen peroxide on the corresponding carboxylic acid in the presence of a weak acid catalyst, with continuous elimination of water by azeotropic entrainment, characterized in that the molar ratio of cyclohexanone used to the percarboxylic acid is between about 0.50 to 0.99.

4 Claims, 1 Drawing Sheet

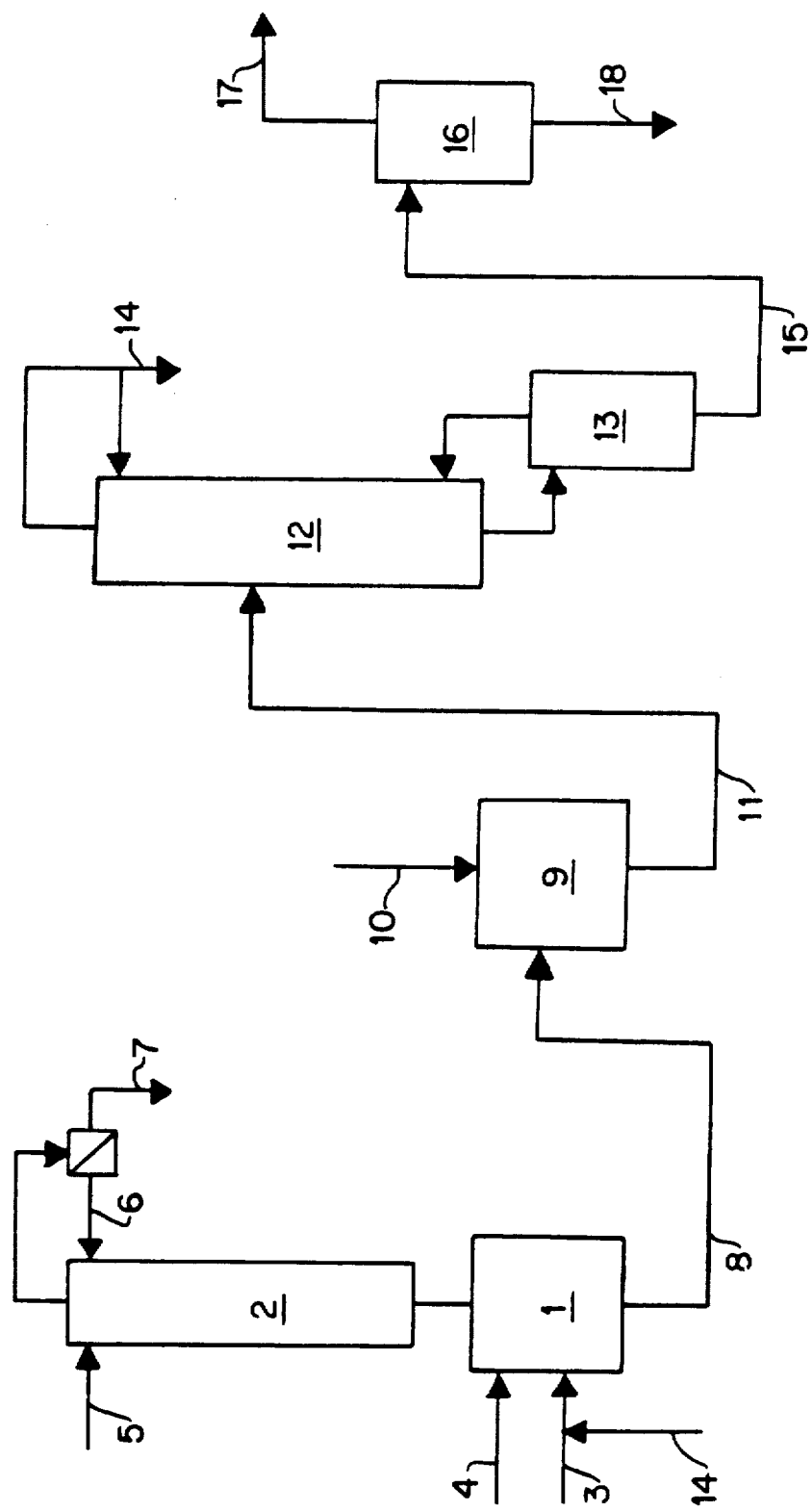

PROCESS FOR THE PREPARATION OF EPSILON-CAPROLACTONE

This application is a continuation of application parent Ser. No. 06/929,888, filed Nov. 13, 1986, which is a continuation of application Ser. No. 06/653,667, filed Sept. 21, 1984, which is a continuation of application Ser. No. 06/457,914, filed Jan. 14, 1983, each of which is abandoned.

TECHNICAL FIELD

This invention relates to a process for the preparation of Σ-caprolactone by means of the oxidation of cyclohexanone with a crude solution of percarboxylic acid.

BACKGROUND ART

Since its discovery in 1899, it has been well known that via the Baeyer-Villiger reaction, ketones may be oxidized to esters by means of a percarboxylic acid. The mechanism of the reaction is such that a complex peroxidized intermediary is formed and subsequently rearranges itself according to an ionic process to yield an ester.

A particularly important application of the Baeyer-Villiger reaction is in the preparation of lactones from cyclic ketones. When the cyclic ketone cyclohexanone is oxidized by percarboxylic acid, Σ-caprolactone is formed.

In U.S. patent application Ser. No. 345,240, filed Feb. 3, 1982, direct use of crude percarboxylic acid solutions, such as crude perpropionic acid solutions for the oxidation of cyclohexanone is disclosed. These crude solutions are obtained according to the method described in U.S. Pat. No. 4,338,260 issued July 6, 1982 and of common assignee.

This method consists of causing the hydrogen peroxide to react with a water miscible carboxylic acid in the presence of a weak acid (boric acid) as a catalyst, while continuously eliminating the water from the reaction medium by azeotropic distillation using an inert organic solvent, such as dichloro-1,2-ethane. An improvement in this method, consisting of injecting water into the azeotropic distillation column, is described in French patent application No. 82 00407, dated Jan. 13, 1982. This improved method is described in Examples 2 and 3 below.

When the crude percarboxylic acid solutions thus obtained are used according to the teaching in U.S. Pat. application Ser. No. 345,240 for the oxidation of cyclohexanone, a molar ratio of cyclohexanone to percarboxylic acid between 1 and 5, and preferably between 1 and 1.5, is used. Under these conditions, yields of Σ-caprolactone are obtained in the order of 92% in relation to the peroxidic oxygen used.

The Kinetic study of the reaction between cyclohexanone and peracetic acid, undertaken by V. M. Vishnyakov et al. (JOURNAL OF APPLIED CHEMISTRY, USSR, Vol. 49, No. 9, p. 2035, 1976) showed that it was a bimolecular reaction of the first order with regard to each of the reagents. However, the prior art concerning the oxidation of cyclohexanone by peracids has always recommended using an excess of ketone in relation to the peracid. This excess of ketone is used as a dilutant for the reaction and avoids the annoying formation of peroxides which present a serious explosive danger.

Thus, molar ratios from 2 to 15 of cyclohexanone to peracid have been recommended whatever method of preparing percarboxylic acid is used:

aqueous solutions of peracid (Japanese patent application 45-15737/1970 and German Federal Republic patent No. 1,258,858).

peracid formed in situ by co-oxidation of cyclohexanone and acetaldehyde (K. Tanaka et al., Kogyo Kagaku Zasshi, 73, p. 943, 1970)

anhydrous organic solutions of peracid (P.S. Starcher, JACS, 80, p. 4079, 1958)

Although the use of a molar excess of cyclohexanone in relation to percarboxylic acid frequently has certain advantages from the point of view of ease and safety of operation, this method, on the other hand, has the disadvantage of requiring, after the oxidation reaction, the separation by distillation of residual cyclohexanone for its recycling.

In the case where the percarboxylic acid used is perpropionic acid, as in Federal Republic of Germany Patent No. 2,920,436, it is also necessary to effect the separation by distillation of cyclohexanone and propionic acid, each of these reagents being recycled at a different stage of the process. The existence of an azeotrope under reduced pressure between cyclohexanone and propionic acid makes this separation that much more difficult since they are compounds whose boiling points are very close. For example, under pressure of 100 mm mercury (13.3 kPa), the boiling points are as follows:

| Propionic acid | 86° C. |
|---|---|
| Cyclohexanone | 93° C. |
| Azeotrope | 93° C. |

On the other hand, it is not possible to effect this separation of propionic acid and cyclohexanone at ordinary pressure because the cyclohexanone condenses easily on itself under the effect of high temperature an also under the influence of various catalysts, especially acids, as shown by C. D. Hurd (JACS, 61, p. 3359, 1939). Among the products of condensation, there is notably formed a dimer, made up of a mixture of two isomers, cyclohexene-1-yl-2-cyclohexanone and cyclohexylidene-2-2cyclohexanone. Thus, at high temperatures, these by-products would then be found as impurities in ε-caprolactone.

While pursuing research on the applications of crude percarboxylic acid organic solutions obtained according to U.S. Pat. No. 4,338,260, the applicants discovered that, contrary to everything taught by the prior art, it is possible to effect the oxidation reaction of cyclohexanone by these crude peracid solutions by using an excess of peracid in relation to cyclohexanone, while conserving a high selectivity in relation to the ketone and peroxidic oxygen used and avoiding the formation of unsafe peroxides. This is possible because the peracid organic solution used by the applicants is practically anhydrous and devoid of all traces of a strong acid catalyst, such as sulfuric acid. Practically or substantially, anhydrous means that there is insufficient water present to adversely affect the reaction.

After the oxidation stage, the separations of the different constituents of the reaction mixture are made without any significant loss of residual peroxidic oxygen. As the engaged cyclohexanone is practically entirely consumed in the oxidation reaction, the top fraction obtained in the distillation of the crude oxidation products can be directly recycled at the stage of synthesis of the peracid solution. The bottom fraction, constituted essentially of Σ-caprolactone, is advantageously purified in a simple later distillation.

Thus, the advantage of the process of the invention is to provide very good yields of Σ-caprolactone with very low energy consumption in a simple and efficient manner.

The oxidation reaction of cyclohexanone by the crude peracid solution is achieved preferably at atmospheric pressure, but can also occur at lower or higher pressure. The temperature of the reaction is between about 20° and 120° C., and preferably between about 40° and 80° C.

The molar ratio of cyclohexanone used to percarboxylic acid is about 0.50 to 0.99, and preferably between about 0.75 and 0.90.

The reaction can be carried out batchwise or continuously. In the latter case, one or more reactors are fed by cascading cyclohexanone and crude percarboxylic acid solution simultaneously. The duration is between 30 min. and 4 hrs. depending on the temperature chosen for the reaction.

At the end of the oxidation, the reaction products are separated by distillation using the usual techniques. On the one hand, residual percarboxylic acid and the mixture of carboxylic acid and the entraining azeotropic solvent, and on the other hand the produced caprolactone are recovered. The distillations are advantageously carried out under reduced pressure to limit the losses of peroxidic oxygen and the thermal degradation of Σ-caprolactone. Preferably, evaporators currently in industrial use are employed, such as thin layered evaporators or film evaporators.

The following examples illustrate various aspects of the invention but the invention is not limited to them. In these examples, the amounts of Σ-caprolactone and cyclohexanone of the final solutions are determined by chromatography in the gaseous phase while the residual peroxidic oxygen is determined chemically.

EXAMPLE 1

A crude solution of perpropionic acid is prepared in accordance with U.S. Pat. No. 4,338,260, by the reaction of hydrogen peroxide in an aqueous solution of 70% by weight $H_2O_2$ with the propionic acid in the presence of 1% weight of orthoboric acid while continually eliminating the water in the reaction medium by azeotropic entrainment with dichloro-1,2-ethane.

The crude solution obtained has the following composition by weight:

| | |
|---|---|
| dichloro-1,2-ethane | 16.0% |
| propionic acid | 59.9% |
| perpropionic acid | 22.8% |
| hydrogen peroxide | 0.3% |
| orthoboric acid | 1.0% |

150.7 g. of this crude perpropionic acid solution are placed in a 250 cm³ glass reactor equipped with an agitation system, a refrigerant and a temperature control system. The reactor is brought to a temperature of 50° C., then 33.6 g. of cyclohexanone, 0.86 mole per mole of peroxidic oxygen, are introduced over a period of 30 minutes.

After 3 hours of reaction, the agitation is stopped and the reactor is cooled. A solution is drawn off having the following by weight composition:

| | |
|---|---|
| dichloro-1,2-ethane | 13.6% |
| propionic acid | 62.0% |
| cyclohexanone | 0.4% |
| Σ-caprolactone | 20.4% |
| perpropionic acid | 2.8% |
| boric acid | 0.8% |

The conversion rate of cyclohexanone is 98%. The selectivity of Σ-caprolactone is 97.5% in relation to cyclohexanone and 96% in relation to the engaged peroxidic oxygen.

EXAMPLE 2

Example 1 is repeated, but using for the preparation of the crude perpropionic acid solution, a mixture recovered by distillation of the products of the reaction of a preceding cyclohexanone oxidation operation.

Thus, 630 g. of a solution having the following compositions by weight are placed in a one liter glass reactor, supplied with an agitation system and equipped with a distillation column of 15 Oldershaw plates and a reflux condenser:

| | |
|---|---|
| dichloro-1,2-ethane | 16.4% |
| propionic acid | 79.5% |
| cyclohexanone | 0.2% |
| perpropionic acid | 2.9% |
| boric acid | 1.0% |

This solution is brought to boiling at reflux under pressure of 100 mm mercury (13.3 KPa) and 92 g. hydrogen peroxide, in the form of a 70% by weight aqueous solution, are introduced over a period of 20 minutes. The organic phase of the water dichloro-1,2-ethane heteroazeotrope is condensed, decanted and refluxed into the distillation column. Simultaneously, 17.5 g/h of water are injected at the top of the column over a period of 2 hours. The temperature in the reactor is 68° C. After 2 hours 30 minutes of reaction, the agitation and heating of the reaction mixture is stopped. The aqueous phase from the condensation and decantation of the heteroazeotrope, drawn away continuously during the entire duration of the operation, weighs 114 g. and contains 0.2% by weight of hydrogen peroxide, approximately 0.3% of engaged peroxidic oxygen.

The crude perpropionic acid solution obtained contains 26.3% by weight of peracid and 0.3% by weight of residual hydrogen peroxide.

600 g. of this solution is placed in a one liter glass reactor, supplied with an agitation system, a refrigerant and a temperature regulation system. The temperature of the reactor is brought to 50° C., then 143 g. of cyclohexanone, about 0.8 mole per mole of engaged peroxidic oxygen, are introduced over a period of 30 minutes. After two hours of reaction the agitation is stopped and the reactor is cooled.

The solution obtained contains mainly 20.8% by weight of Σ-caprolactone and 4.6% residual perpropionic acid. The selectivity of Σ-caprolactone in relation to cyclohexanone is 99%.

EXAMPLE 3

A process for preparing Σ-caprolactone using the installation illustrated in the accompanying drawing is carried out as follows:

(a) In a one liter glass reactor (1) equipped with a distillation column (2) having 15 Oldershaw plates and a reflux condenser, 636 g. of a solution (3) having the following, by weight, composition are introduced:

| | |
|---|---|
| dichloro-1,2-ethane | 19.8% |
| propionic acid | 79.2% |
| orthoboric acid | 1.0% |

This mixture is brought to a boil at reflux under pressure of 100 mm mercury (13.3 KPa) and 92 g. of an aqueous solution (4) 70% by weight hydrogen peroxide, also containing 0.7% by weight of dipicolinic acid stabilizer are introduced over a period of 20 minutes. Simultaneously, 21 g/h of water are injected at the top of the distillation through inlet 5 column over a period of 2 hours 30 minutes. The temperature of the reactor is 65° C. The condensed organic phase of the heteroazeotrope is recycled in (6) to insure the reflux. The condensed aqueous phase is decanted and continuously drawn out through the outlet (7). The reaction is stopped after 3 hours.

The crude peracid solution drawn out through line (8) contains 23.7% by weight of perpropionic acid which represents a transformation rate of 92% in relation to the engaged hydrogen peroxide.

(b) The crude peracid solution is sent into a reactor (9) where cyclohexanone is introduced over a period of 30 minutes through line (10) in such quantity that the molar ratio of cyclohexanone to perpropionic acid is 0.83. After 2 hours, 30 minutes, of reaction at 50° C. (This time includes the 30 minutes of time for the introduction of cyclohexanone) a crude caprolactone solution is obtained having the following by weight composition:

| | |
|---|---|
| Σ-caprolactone | 19.8% |
| dichloro-1,2-ethane | 13.8% |
| propionic acid | 62.6% |
| perpropionic acid | 3.6% |
| cyclohexanone | 0.4% |

The conversion of cyclohexanone is thus 97%. The selectivity of Σ-caprolactone is 96% in relation to cyclohexanone and 92% in relation to perpropionic acid.

(c) This crude Σ-caprolactone solution is introduced continuously at the rate of 365 g/hour through line (11) into a distillation column (12) equipped with 25 Oldershaw plates and functioning under pressure of 10 mm mercury (1.33 KPa). This column is equipped with a film evaporator (13) functioning as a distiller. The temperature is 33° C. at the top of the column and 141° C. at the bottom. The reflux rate used is 0.15. After condensation at the head of the column, 290 g/h of a solution containing 73.4% by weight of propionic acid, 16.3% by weight of dichloro-1,2-ethane and 4% by weight of perpropionic acid are drawn off through line (14). This solution can be directly recycled at the synthesis stage (a) of the peracid. The recovery rate of peroxidic oxygen is 93% in this distillation.

(d) 75 g/h of a solution containing 93.7% Σ-caprolactone and less than 100 ppm cyclohexanone and less than 700 mm of propionic acid are drawn off continuously from the bottom of column (15).

This solution is purified by simple evaporation under reduced pressure of 10 mm mercury (1.33 KPa) in a film evaporator (16), identical to evaporator (13). The bottom fraction is eluminated through line (18) and Σ-caprolactone is collected at (17) whose strength of 99.3% by weight matching the commercial specifications in use.

We claim:

1. A continuous process for manufacturing epsilon-caprolactone which comprises:

reacting a $C_2$–$C_4$ carboxylic acid with hydrogen peroxide in the presence of a boric acid catalyst and an azeotropic solvent in a first reaction vessel to form a crude percarboxylic acid solution containing a $C_2$–$C_4$ percarboxidic acid and unreacted carboxylic acid, hydrogen peroxide, catalyst and solvent, while continuously eliminating the water of reaction by azeotropic entrainment with said solvent;

directing said crude percarboxylic acid to a second reaction vessel to form a reaction mixture with cyclohexanone wherein the molar ratio of cyclohexanone to percarboxylic acid is maintained at between 0.75 and 0.9 for oxidizing cyclohexanone to epsilon-caprolactone;

directing said reaction mixture to a column for separation of a crude epsilon caprolactone solution from said crude percarboxylic acid solution;

recycling said separated crude percarboxylic acid solution to said first reaction vessel; and recovering epsilon caprolactone by distillation under reduced pressure of said crude epsilon caprolactone solution.

2. The method of claim 1 wherein the percarboxylic acid is perpropionic acid.

3. The method of claim 1 wherein the azeotropic solvent is dichloro-1, 2-ethane.

4. A continuous process for manufacturing epsilon-caprolactone which comprises:

reacting propionic acid with hydrogen peroxide in the presence of a boric acid catalyst and an azeotropic solvent comprising dichloro-1, 2-ethane in a first reaction vessel to form a crude perpropionic acid, unreacted propionic acid, hydrogen peroxide, catalyst and solvent, while continuously eliminating the water of reaction by azeotropic entrainment with said solvent;

directing said crude perpropionic acid to a second reaction vessel to form a reaction mixture with cyclohexanone wherein the molar ratio of cyclohexanone to perpropionic acid is maintained at between 0.75 and 0.9 for oxidizing hexanone to epsilon-caprolactone;

directing said reaction mixture to a column for separation of a crude epsilon-caprolactone solution from said crude perpropionic acid solution;

recycling said separated crude perpropionic acid solution to said first reaction vessel; and recovering epsilon-caprolactone by distillation under reduced pressure of said crude epsilon-caprolactone solution.

* * * * *